United States Patent [19]

Kempe

[11] Patent Number: 4,825,877
[45] Date of Patent: * May 2, 1989

[54] METHOD OF PAIN REDUCTION USING RADIATION-SHIELDING TEXTILES

[76] Inventor: Frieder K. Kempe, 2002-1055 West Georgia Street, Vancouver, B.C., Canada, V6E 3P3

[*] Notice: The portion of the term of this patent subsequent to Mar. 31, 2004 has been disclaimed.

[21] Appl. No.: 32,832

[22] Filed: Mar. 30, 1987

Related U.S. Application Data

[63] Continuation-in-part of Ser. No. 602,592, Apr. 20, 1984, Pat. No. 4,653,473.

[51] Int. Cl.$^4$ .............................................. A61N 1/16
[52] U.S. Cl. .................................... 128/846; 128/898; 139/425 R; 361/220
[58] Field of Search ................ 128/1 R, 82.1, 132 IR, 128/165, 362, 379–382, 384, 419 R, 846, 897, 898; 2/1, 16, 22, 69, 69.5, DIG. 7; 361/220, 223, 224; 174/55 B; 139/425 R; 54/79

[56] References Cited

U.S. PATENT DOCUMENTS 3,699,590 10/1972 Webber et al. ................ 261/220 X
4,398,277 8/1983 Christiansen et al. .............. 361/220

FOREIGN PATENT DOCUMENTS

82/02148 7/1982 PCT Int'l Appl. ................ 128/1 R
777771 6/1957 United Kingdom .............. 128/1 R
2025237 1/1980 United Kingdom ............ 128/132 R

*Primary Examiner*—Lee S. Cohen
*Attorney, Agent, or Firm*—Chernoff, Vilhauer, McClung & Stenzel

[57] ABSTRACT

A method of reducing pain resulting from exposed or damaged nerve ends, such as the pain in amputees commonly referred to as phantom limb pain is disclosed. The method may also reduce pain resulting from arthritis. This method involves covering the affected area with a radiation-shielding textile, whether by fashioning a garment from the textile or using a sheet or cover. The radiation-shielding textile found to be suitable is a cloth woven of yarn consisting of a textile fibre, such as nylon, and from two to thirty-five percent by weight of conductive metal filament. A method of relieving muscle soreness, improving the healing of injuries and reducing nervousness in animals, particularly horses, is also disclosed.

3 Claims, 2 Drawing Sheets

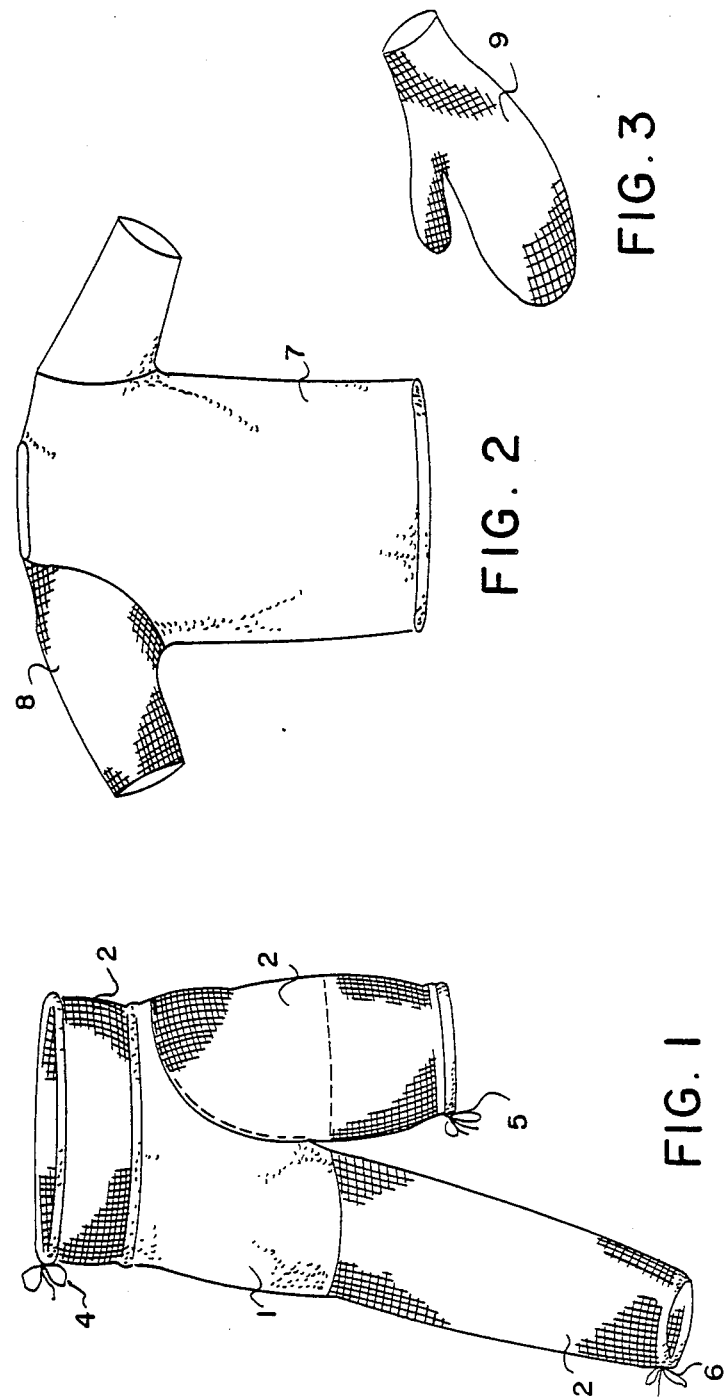

METHOD OF PAIN REDUCTION USING RADIATION-SHIELDING TEXTILES

BACKGROUND OF THE INVENTION

This application is a continuation-in-part of application ser. No. 602,592 filed Apr. 20, 1984, now U.S. Pat. No. 4,653,473.

FIELD OF THE INVENTION

The present invention relates to methods of pain treatment. In particular, it relates to a method for reducig phantom limb pains, stump pains and stump spasms in amputees, arthritic pains and other pains related to severed or damaged nerve endings. It further relates to a method of reducing muscle pain, improving healing and promoting relaxation in animals, particularly horses.

DESCRIPTION OF THE PRIOR ART

The phenomenon of phantom limb sensation and phantom limb pain has been documented for several years, but the cause of the phenomenon has not been adequately explained. According to this phenomenon, an amputee will have a sensation of pain in a limb or extremity despite the fact that the actual limb or extremity has been amputated. Such pains may be persistent and severe and may disrupt the sufferer's sleep. Up to the present, the only effective treatment for such pains has been by the use of pain-killing drugs. Surgical treatment of the nerves in the stump, ultrasound and hot wax treatments, physiotherapy and injections of sclorosing or anesthetic agents have all been tried without success.

According to one theory, the nervous system is normally shielded by a healthy layer of skin from electro-magnetic radiation or random electric currents, whether from the sun or other sources both natural and manmade. In the case of an amputee, part of the layer of skin is destroyed and is replaced by scar tissue, and nerve ends are thereby exposed to electromagnetic radiation or random electric currents. The nerve itself may have been severed, leaving it more susceptible to the effects of radiation. A possible effect of radiation impinging on the nerve end is to generate an electrical signal in the nerve which is interpreted by the brain as a pain signal from the amputated limb.

The concept of electromagnetic shielding is well known. A sheet of conductive material placed between points A and B serves to shield point A from changes in an electromagnetic field occuring at B. The same effect is approximated when a grid or network of conductors is substituted for the sheet of conductive material. Such a grid is sometimes referred to as a Faraday cage, particularly when an object is completely surrounded by such grid to shield it from changing electromagnetic fields. For example, a grounded Faraday cage may be used to shield an object from lightning.

Textile materials which are partly woven from metallic fibers are well known for various uses. One reason for including metallic fibers in textiles has been the esthetic appearance of the fabric. Textiles containing metal fibers have also been used to increase the strength and resistance to stretching of the fabric, to provide a heat reflecting fabric for use in protective clothing, or to form an electrically conductive fabric for use in clothing to reduce the build-up of static charges and avoid the dangers created by static dischrages through sparking. Various methods are known for manufacturing such textiles. One known method is to weave the textile from a yarn composed of a relatively small quantity of metal filaments, whether continuous or discontinuous, along with the textile fiber.

SUMMARY OF THE INVENTION

The present invention provides a method of alleviating pain resulting from exposed or damaged nerve ends such as the phantom limb pain in amputees by shielding the scarred stump area from electromagnetc radiation. The method comprises the step of shielding the stump or arthritic area with a cloth woven from a yarn containing threads of a conductive metal. Such method has also been found to be effective to reduce stump spasms and stump pains in amputees, pain from scars other than those resulting from amputation and also arthritic pain and menstrual pain and cramps. The yarn is preferably composed of from 2 to 35% by weight of conductive metal filment, and the balance of natural or synthetic textile fiber such as nylon. The metal may be any conductor, but a stainless steel alloy has been found to be effective.

The present invention also provides a method of relieving muscle pain and soreness, promoting healing and reducing nervousness in animals, particularly horses. The invention comprises the steps of shielding the painful or injured area with a cloth woven from a yarn containing threads of conductive metal. The yarn is preferably composed of from 2 to 35% of a conductive metal filament, preferably a stainless steel alloy, and the balance of a natural or synthetic fibre such as nylon. A blanket may also be fashioned from the cloth and worn as a horse blanket to reduce muscle soreness in the animal's back area and generally reduce nervousness.

BRIEF DESCRIPTION OF THE DRAWINGS

In drawings which illustrate embodiments of the invention:

FIG. 1 illustrates leggings to be worn by a leg amputee according to the method of the invention;

FIG. 2 illustrates a shirt which may be used also according to the method of the present invention;

FIG. 3 illustrates a mitt of a type used according to the method of the invention.

DETAILED DESCRIPTION OF AN EMBODIMENT OF THE INVENTION

Figure 4:
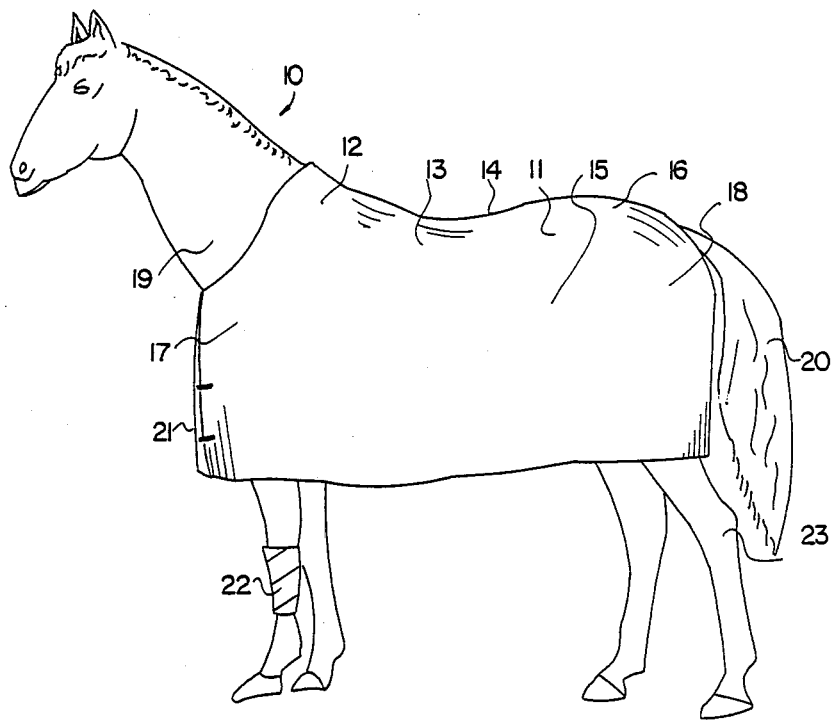
FIG. 4 illustrates a horse wearing a blanket and a leg bandage of a type used according to the method of the invention.

At the basis of the present invention is the discovery that phanton limb pains, stump pains, stump spasms and scar pains in amputees may be reduced or eliminated by covering the stump or scarred area with an appropriate metallic cloth. Apparently the cloth acts much as a Faraday cage to shield the scarred area from changing electromagnetic fields or random electric currents which otherwise would stimulate unprotected nerve endings resulting in phantom limb pains.

According to the method of the invention, the scar tissue on the stump should be covered with one or more layers of the appropriate metallic cloth, so that the cloth overlaps the scarred area. Direct skin contact is not required. A suitable method of covering the affected area is to fashion a piece of clothing partly from the metallic cloth material so that the amputee may, by wearing the article of clothing, cover the stump area and any other scar tissue with the metallic cloth. For example, FIG. 1 shows pants or leggings 1 which have been successfully used by an amputee whose left leg had been amputated five inches below the groin. The shaded areas 2 constitute the appropriate metallic cloth. th. In this case, the amputee also had a shrapnel wound in the right knee, and an abdominal scar resulting from an appendectomy. A drawstring is provided at 5 to complete the coverage of the left stump. A drawstring was also provided at 6 to tighten the coverage of the material around the scarred area on the right knee. Similarly a drawstring at 4 was provided to complete the coverage of the abdominal scar area. FIG. 2 shows a short-sleeved shirt 7 which is partly sewn using the appropriate metallic cloth 8 in an area to reduce either phantom limb pain in the case of a person whose right arm has been amputated, or arthritic pain in the case of an arthritic afflicted in the right shoulder. Where one or more fingers have been amputated, or the person suffers from arthritis in the joints of the hand, a mitt 9 may be completely sewn from the appropriate metallic cloth as shown in FIG. 3.

The method of the present invention has also been found to alleviate menstrual pains and cramps. Such pains and cramping may occur periodically in females and may be quite debilitating. The patient's sleep may be disturbed. It has been found tht wrapping the suitable metallic cloth around the lower body while sleeping considerably alleviates such pain and cramping and permits uninterrupted sleep.

For complete relief, the article of clothing is worn both day and night, or whenever the pain recurs. Where the main problem is pain-induced disruption of sleep, the article of clothing may only be worn at night. Alternatively, a bed sheet composed of the appropriate metallic cloth will also reduce the pain.

A suitable cloth for the practice of the method of the invention which both provides the appropriate electromagnetic shielding and the comfort of a standard non-metallic textile is a fabric sold under the trade mark FARABLOC. The yarn from which the textile is woven is composed of approximtely 13% by weight of stainless steel filaments. The balance of the yarn is a synthetic nylon fiber such as nylon 66. The yarn has an electrical conductance of approximately 330 ohms per centimeter The fabric has a warp of 24.5 threads per centimeter and a woof of 24.5 threads per centimeter. The weight of the fabric is approximately 200 grams per square meter. The binding is L 1/1—that is, one thread up and one thread down. Other conductive metals would be suitable, such as copper or silver. Other natural or synthetic fibers would also be suitable to comprise the yarn. It would also be suitable to utilize cloth woven of alternate threads of metal and textile fiber.

Case Study 1

The end of the index finger on the right hand of the patient had been sheared off in an industrial accident. A number of operations had removed the stump of the finger. The patient had suffered daily. Chills, throbbing and itching in the area of the amputated finger were experienced and occasional phantom pains which felt like a nail being driven through the amputated finger and the sensation that the finger was being stretched occurred. These sensations occurred mostly at night. Nothing had served to alleviate the phantom pains. On occasion, the whole hand would go into a spasm. Temporary relief of this latter affliction was provided by pain killers, ultrasound therapy and hot wax therapy.

A single mitt as shown in FIG. 3 was fashioned for the patient from the metallic cloth described above. The mitt was worn in the evenings and while driving to work. The patient found that quick and effective relief from the pain resulted from wearing the mitt and the patient was now able to sleep comfortably.

Case Study 2

The patient had been injured in World War II by shrapnel and gun shots resulting in fracture of the left leg and a groin aneurism. Eventually, the left leg was amputated five inches below the groin. Some shrapnel still remained in the right knee. The patient also suffered from arthritis in the right shoulder. The patient suffered from constant phantom limb sensation in the left limb, and periodic excruciating phantom limb pain. Nothing was found to alleviate the phantom limb sensation, although immersion in hot water, massage and pain killing drugs would provide temporary relief from the phantom limb pain. Stump spasms or "stump jump" would also occur periodically. The patient's pajama bottoms were altered by sewing the metallic cloth into the pants as shown in FIG. 1. A portion of the fabric was also sewn into the right shoulder of a t-shirt as shown in FIG. 2. The patient wore the garment over a number of months and during this period suffered no symptoms of phantom limb pains. In addition, the pain in his arthritic shoulder was alleviated. The patient was able to discontinue the use of prescription pain-killing drugs.

Case Study 3

The patient's left leg had been amputated eight inches below the groin as a result of cancer in the calf muscle and knee. The patient suffered daily phantom limb sensation and periodic intense phantom limb pain in the left leg. Massaging the stump would alleviate the phantom limb sensation. Nothing was found to alleviate the phantom limb pain. The patient also suffered from painful "stump jump" periodically, and again nothing was found to relieve the pain. A garment was fashioned having the metallic cloth covering the stump of the patient and the garment was worn when attacks of the pain occurred. The patient found that within ¾ of an hour to one hour of covering the stump with the cloth, the phantom limb pain completely disappeared. During a test period of ten weeks, the garment worked successfully on at least five occasions.

Case Study 4

The patient's left arm was crushed in an industrial accident and the patient was left with heavy scarring and only partial use of the arm. Arthritis developed and the patient suffered severe pain in the arm. His sleep was constantly disturbed. A long sleve of the metallic cloth was sewn onto a t-shirt which the patient wore at night. The patient found that the amount of pain suffered was reduced by at least two-thirds. The disturbance of sleep was reduced and the need for pain killing drugs was almost eliminated.

CASE STUDY 5

The patient was born with a foot deformity which resulted in damage to the knees. Surgery was performed but arthritis eventually developed in the knees. The patient suffered recurring pain in the knees which seriously affected sleep. A piece of the metallic textile was used to cover the knees, and the patient found that the pain was decreased considerably. The disturbance of sleep was eliminated and the amount of pain killing drugs which were required was reduced.

Of the sufferers of chronic pain who hve been tested by the method of the present invention to date, in 12.5% of the cases, the treatment had no noticeable effect. 62.5% of the cases showed successful results from the use of the metallic textile in that the need for analgesics was substantially eliminated. The method has been found to successfully reduce pain in 60 to 70% of cases studied.

The method of the present invention has also been found to alleviate the pain caused by migraine headaches, spinal pains such as intervertebral disk pains and pains resulting from skin burns, including radiation burns. The method of the present invention has also been found to improve the rate of skin regeneration in the case of skin burns, and also enhances blood circulation and muscle relaxation. It has also been found that the radiation-shielding textile should cover the affected area so that it extends at least about fifteen centimetres beyond the edge of the affected area.

A particularly suitable staple fiber yarn for the radiation-shielding textile of the present invention has been found to be one in which the steel and textile fibres are cut to a length of between fifty millimeters and seventy millimeters. It has also been found that a cloth woven of yarn consisting of a textile fibre and approximately 3% by weight of metallic fibres is also suitable for the method of the invention.

Two conductive yarns which are particularly suitable for the radiation-shielding cloth of the present invention are those manufactured under the trade marks BEKITEX H54/1 and BEKITEX H54/2 by Bekaert S.A. of Belgium. These yarns or threads contain BEKINOX (a trade mark of the same company) stainless stel fibres having a thickness of about eight microns. In the case of BEKITEX H54/1, the thickness of the thread is Nm54/1 or 185 dtex. The yarn is a three-cylinder staple fibre yarn whose linear resistance measures 336 ohms per centimetre and the mean length of the concutive zone measures 750 millimeters. In the case of BEKITEX H54/2, the fineness of the threads is Nm 27 or 370 dtex. This yarn is twisted. In this case the linear resistnce is 168 ohms per centimeter. A cloth of BEKITEX H54/2 was found to reflect 92% of an electromagnetic field having a test frequency of 1 GHz when one layer was used and 97.6% when two layers were used. The cloth showed a surface and core resistance of less than 100 ohms.

While it is recognized that other conductive metals could be used in the cloth for the method of the present invention, stainless steel is partcularly suitable as other conductive metals such a copper or aluminum are subject to corrosion and oxidation and would not therefore be suitable for articles of clothing which must be washed in water and which would be exposed to perspiration.

The method of the present invention has also been found to have surprisingly beneficial results in treating thoroughbred horses. FIG. 4 shows a horse 10 wearing a horse blanket 11 of standard design but constructed from the radiation-shielding cloth previously described, such as BEKITEX H54/1 or H54/2. The blanket covers the withers 12, back 13, loin 14, flank 15, croup 16, shoulder 17 and thigh 18 of the horse. The blanket is designed to allow the neck 19 of the horse and tail 20 to extend through apertures in the blanket. For example, the blanket may be joined by clasps along the front edge 21.

Also shown in FIG. 4 is a wrapping or bandage of radiation-shielding textile 22 shown wrapped around the foreleg of the animal to treat an injury.

Case Study 6

An eight-year-old thoroughbread gelding of international competitive class was found to have a chronic muscle soreness problem over a period of two years involving muscles in the shoulder, back, hips and pelvic areas of the horse. Massage treatments and muscle-relaxant drugs were applied without success. The other treatments were stopped, and the method of the present invention was applied for about five days. The horse blanket shown in FIG. 4, constructed of the radiation-shielding cloth of the invention was put on the horse whenever it was not working out or being groomed. No other treatment was used concurrently. Within three days the trainer had noted improvement. The muscle problems were hardly noticeable. Where the muscle areas in the shoulder, back and hip had previously been very tender, the tenderness was no longer present.

The same thoroughbred horse had problems with an old leg injury. The near foreleg had scar tissue across the tendon area as a result of a cut that had required fourteen stitches. The scar tissue formed horizontally across the leg caused the tendon and ankle to fill with fluid. It had previously been necessary to "sweat" the fluid out of the joints every few days using heat-generating ointments. Use of the ointment was discontinued for three days and any such "sweat" had been washed off. A small square of the radiation-shield textile described above was applied over the injury under an oridinary stable bandage. Overnight, the trainer found the swelling to have disappeared, and the fabric appeared to have increased the circulation in the leg.

Case Study 7

A thoroughbred horse was suffering from stiff joints and muscle tightness prior to races. Specifically the tightness occurred in the hook joints, shown in FIG. 4 as 23. The radiation-shielding textile described above was applied by the trainer by wrapping it around each joint and holding it in place with a "hook glove" which is a specially shaped plastic device for holding the bandage on the joint. The textile was put on three hours prior to the race, and after two hours the tightness had been relieved and the horse was able to be taken out for the race. The trainer noted the looseness and mobility of the horse. The trainer also noted that the area where the radiation-shielding textile had been applied was very warm and the horse appeared to be sweating in that area more than it would have with a normal bandage.

Case Study 8

A race horse had a condition referred to as "bow tendon" in the front left leg. This is a condition wherein the tendon is torn in one or more places. Two or three layers of the radiation-shielding textile described above were wrapped around the affected tendon area and were left in place for one and a half weeks. At that time the horse was taken to a verterinarian and the bow tendon condition was examined under ultrasound. The torn tendons were beginning to heal and this was occurring at a rate greater than would have been expected under normal conditions by the veterinarian.

The same horse was a high-strung stallion and the radiation-shielding textile of the invention was used as a horse blanket as shown in FIG. 4 on the horse. The trainer noted within twenty minutes of applying the blanket, the standard signs of calmness of the horse, such as gentle exhaling of air, indicating that the nervousness of the horse had been reduced.

While a woven cloth has been specified in the decription of the prferred embodiment, it will be apparent to those skilled in the art that a non-woven cloth having a grid of conductive metallic filaments will also operate effectively in the method of the invention while retaining the qualities of a non-metallic fabric. As will also be apparent to those skilled in the art in light of the foregoing disclosure, many variations in the type of metallic thread or yarn and textile fibers used in the cloth and in the manner of weaving the cloth are possible in the practice of this invention without departing from the scope thereof. Accordingly, th scope of the invention is to be construed in accordance with the substance defined by the following claims.

I claim:

1. A method of reducing muscle pain and muscle soreness and facilitating healing in non-human animals comprising the step of shielding painful or injured ares with a cloth comprising between two and thirty-five percent by weight of a continuous system of electrically-conductive stainless-steel fibers and the remainder of non-metallic fibers over a period of time sufficient to reduce the said muscle soreness or to improve said healing.

2. The method of claim 1 wherein said animal is a horse.

3. A method of reducing nervousness in a horse comprising fashioning a horse blanket from a radiation-shielding textile comprising between two and thirty-five percent by weight of a continuous system of electrically-conductive stainless-steel fibers and blanketing said horse with said blanket over a period of time sufficient to reduce said nervousness.

* * * * *

UNITED STATES PATENT AND TRADEMARK OFFICE
CERTIFICATE OF CORRECTION

PATENT NO. : 4,825,877
DATED : May 2, 1989
INVENTOR(S) : Frieder K. Kempe

It is certified that error appears in the above-identified patent and that said Letters Patent is hereby corrected as shown below:

| | |
|---|---|
| In the Title: | Change "TEXTILES" to --TEXTILE--. |
| Col. 1, Line 3: | Change "TEXTILES" to --TEXTILE--; |
| Line 12: | Change "reducig" to --reducing--; |
| Line 32: | Change "sclorosing" to --sclerosing--; |
| Line 67: | Change "dischrages" to --discharges--. |
| Col. 2, Line 53: | Change "phanton" to --phantom--. |
| Col. 3, Line 6: | Delete "th."; |
| Line 18: | Delete "in the"; |
| Line 47: | After "centimeter" insert --.--. |
| Col. 4, Line 64: | Change "CASE STUDY 5" to --Case Study 5--. |
| Col. 5, Line 38: | Change "stel" to --steel--; |
| Line 43: | Change "concutive" to --conductive-- |
| Line 47: | Change "resistnce" to --resistance--. |
| Col. 6, Line 40: | Change "," to --.--; |
| Line 45: | Change "hook" to --hock--; |
| Line 48: | Change "hook" to --hock--; |
| Line 66: | Change "verterinarian" to --veterinarian--. |

UNITED STATES PATENT AND TRADEMARK OFFICE
CERTIFICATE OF CORRECTION

PATENT NO. : 4,825,877
DATED : May 2, 1989
INVENTOR(S) : Frieder K. Kempe

It is certified that error appears in the above-identified patent and that said Letters Patent is hereby corrected as shown below:

Col. 7, Line 22:   Change "th" to --the--.

Signed and Sealed this

Fourth Day of June, 1991

Attest:

HARRY F. MANBECK, JR.

*Attesting Officer*   *Commissioner of Patents and Trademarks*